United States Patent [19]

Pfost et al.

[11] Patent Number: 4,790,183

[45] Date of Patent: Dec. 13, 1988

[54] ACOUSTIC IMPEDANCE SYSTEM FOR LIQUID BOUNDARY LEVEL DETECTION

[75] Inventors: Dale R. Pfost, San Carlos; R. Fred Pfost, Los Altos; Eric W. Lachenmeier, San Jose, all of Calif.

[73] Assignee: Beckman Instruments, Inc., Fullerton, Calif.

[21] Appl. No.: 47,043

[22] Filed: May 5, 1987

[51] Int. Cl.⁴ .............................................. G01F 23/00
[52] U.S. Cl. ................................... 73/290 V; 367/908
[58] Field of Search ............... 73/290 V, 290 R, 584, 73/589, 599, 628; 340/618, 621; 367/908

[56] References Cited

U.S. PATENT DOCUMENTS

| | | | |
|---|---|---|---|
| 2,808,581 | 10/1957 | Findlay | 73/290 V |
| 3,474,902 | 10/1969 | Putman | 73/290 R |
| 3,825,025 | 7/1974 | Samuel et al. | 73/290 V |
| 3,834,233 | 9/1974 | Willis et al. | 73/290 V |
| 4,175,441 | 11/1979 | Urbanek et al. | 73/599 |
| 4,189,722 | 2/1980 | Lerner | 73/290 V |
| 4,320,659 | 3/1982 | Lynnworth et al. | 73/589 |
| 4,474,061 | 10/1984 | Parker | 73/290 V |
| 4,478,094 | 10/1984 | Salomaa et al. | 73/864.14 |

FOREIGN PATENT DOCUMENTS 2241080  3/1975  France ............................. 367/908

Primary Examiner—Stewart J. Levy
Assistant Examiner—Hezron E. Williams
Attorney, Agent, or Firm—William H. May; Paul R. Harder; Thomas Schneck

[57] ABSTRACT

A liquid boundary level detector employing an open-ended conduit which directs pressure waves toward a liquid boundary layer. The conduit is moved from a starting position toward the liquid boundary and, upon contact with the boundary, there is a change in acoustic impedance within the conduit. This change is monitored and a signal is generated indicative of such contact. Once the initial liquid boundary position is determined, that may become the reference position for subsequent liquid boundary measurements or motions.

21 Claims, 2 Drawing Sheets

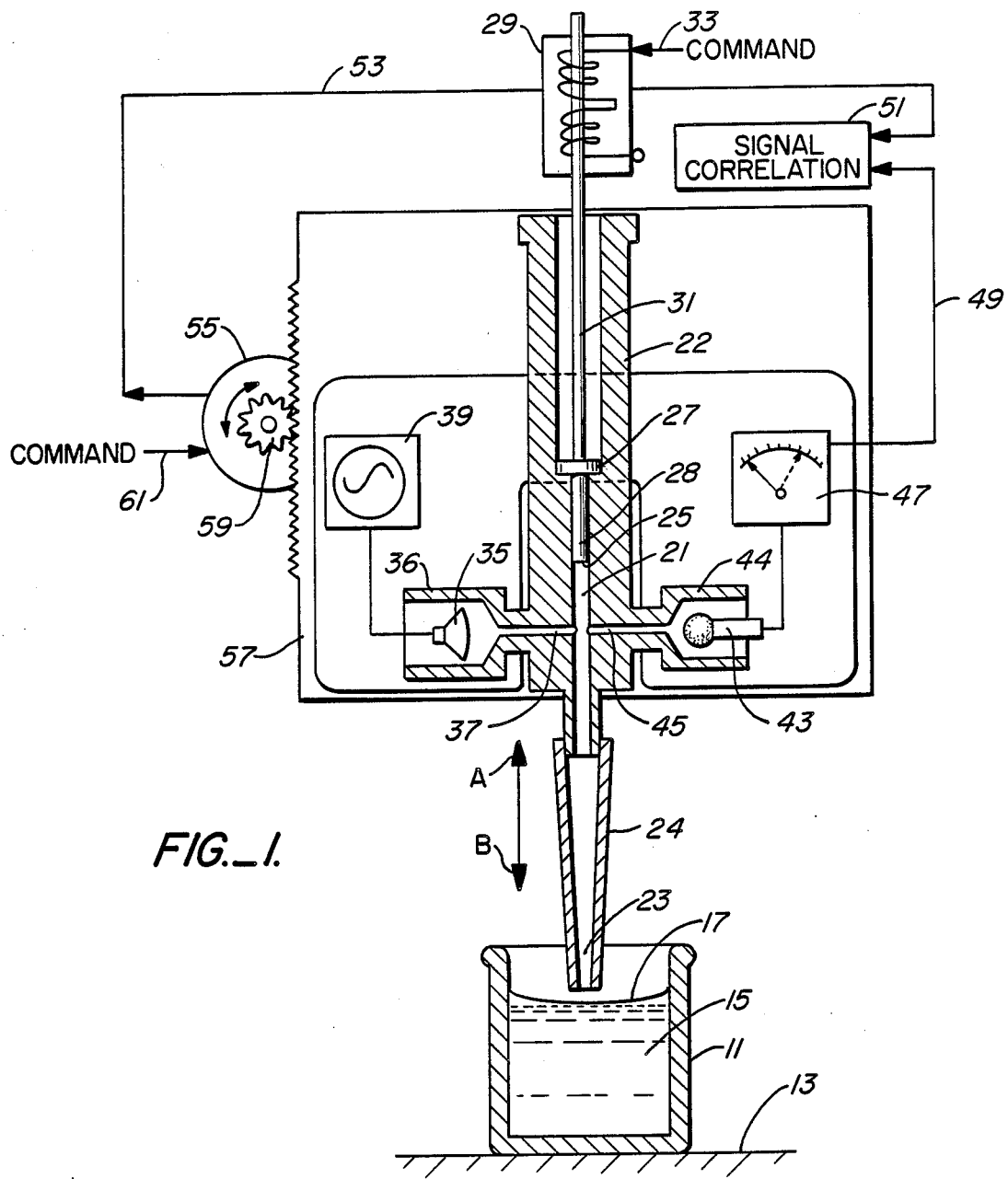
FIG._1.
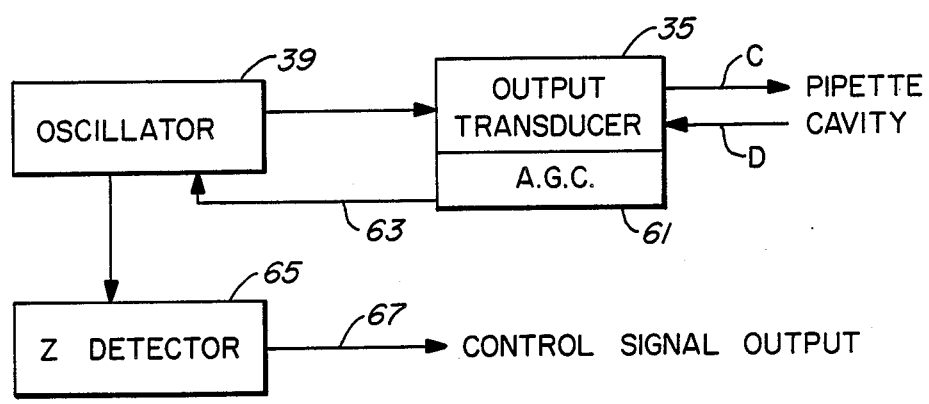
FIG._2.

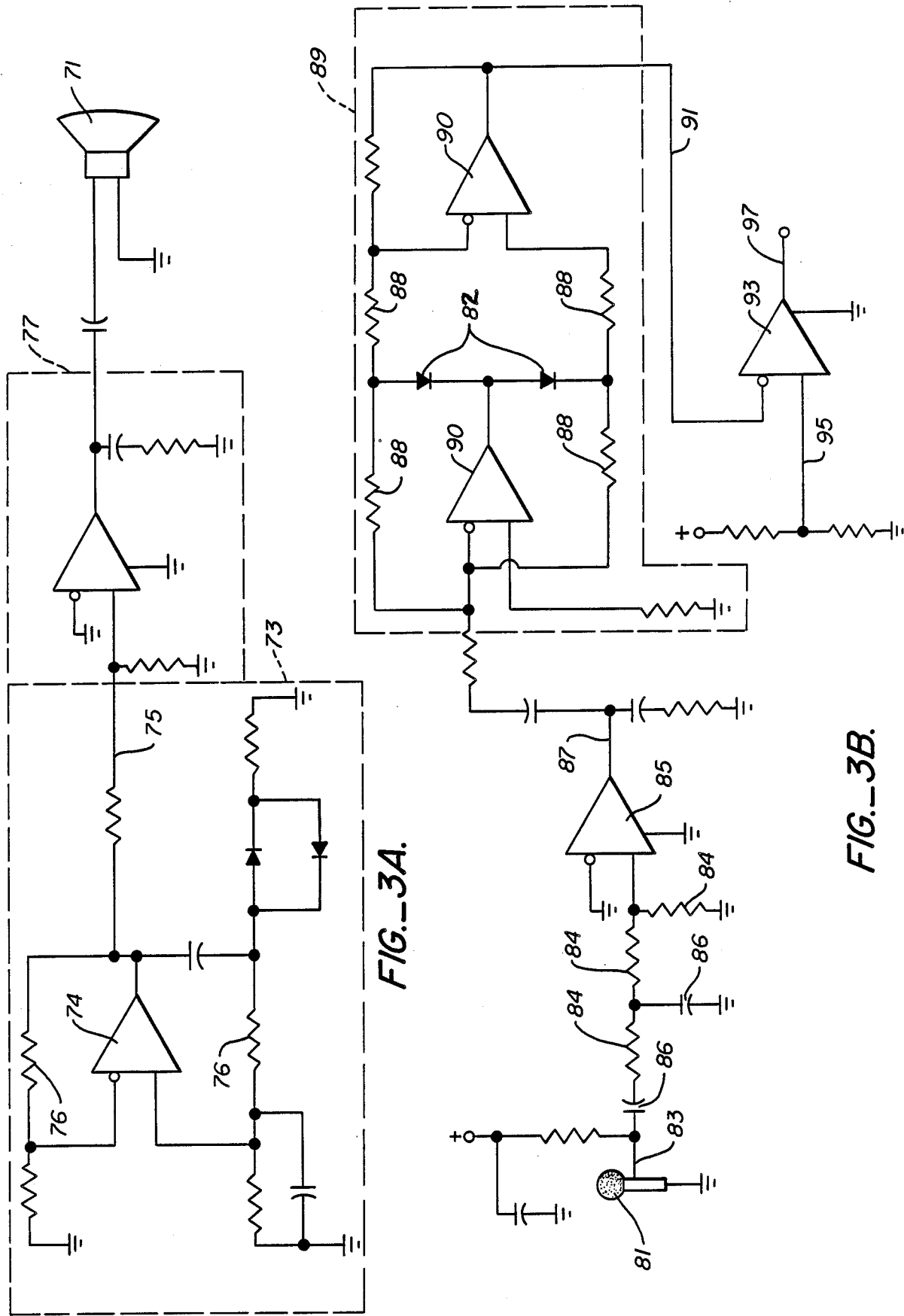

ACOUSTIC IMPEDANCE SYSTEM FOR LIQUID BOUNDARY LEVEL DETECTION

DESCRIPTION

1. Technical Field

The invention relates to apparatus for detecting contact between a liquid boundary and a movable conduit.

2. Background Art

U.S. Pat. No. 4,422,151 to Gilson discloses an automatically manipulated liquid handling tube suitable for dispensing or sampling in horizontal or vertical directions with respect to an array of test tubes or similar containers.

U.S. Pat. No. 4,478,094 to Salomaa discloses a liquid sample handling system which performs predetermined serial dilution by means of an automatic liquid transfer system using a fixed open loop control system.

In most prior art automated liquid handling systems, such as those described in the above patents, the position of a liquid level is either known or determinable. For example, capacitance or conductive probes can be used to find liquid level. However, as samples are removed from containers, liquid levels change, or must be remeasured for other reasons. In these situations, it is desirable to gauge or measure the liquid boundary position.

An object of the present invention was to devise apparatus for measuring contact between a liquid handling conduit, such as a pipette, and a liquid boundary so that liquid level may be ascertained.

SUMMARY OF INVENTION

In music, it is known that there is a substantial change in vibrational modes between an open organ pipe and a closed one. If both ends of a pipe or conduit are closed, and acoustic waves are introduced, the waves must be reflected from the closed ends, known as nodes. An open end, on the other hand, has no such restriction and is known as an anti-node. The present invention relies upon the establishment of acoustic vibrations in an open ended conduit, i.e. one having an anti-node, and then detecting a change in acoustic impedance when the anti-node becomes a node by entry into a liquid boundary which closes the open end of the conduit.

Pressure waves are introduced into a conduit by means of a hollow tube leading into a side wall of the conduit. When an open ended conduit is moved into a liquid boundary, the amplitude or wavelength or frequency or phase of the acoustic waves changes, i.e. there is a characteristic change in acoustic impedance, and this change may be detected with an electrical circuit. The waves which are used are continuous waves, not of the pulse-echo type. Once the change in acoustic impedance occurs, contact with a liquid boundary is established. By monitoring changes in the relative position of the conduit when contact with the liquid boundary is established, changes in height of the liquid boundary are monitored.

BRIEF DESCRIPTION OF THE DRAWINGS

FIG. 1 is a side plan view of the apparatus of the present invention.

FIG. 2 is a simplified electrical schematic for a single transducer embodiment of detection circuits employed with the apparatus of FIG. 1.

FIGS. 3A and 3B are detailed electrical schematics of a two transducer version of the circuits of FIG. 2.

BEST MODE FOR CARRYING OUT THE INVENTION

With reference to FIG. 1, container 11 is shown resting on surface 13 in a known position The container 11 may be a cuvette, vial, beaker or other liquid sample container. The container need not be a laboratory container, but may be a large industrial chemical process tank. The container contains a liquid 15 to be dispensed or handled. A liquid boundary layer 17 defines the upper surface of the liquid, separating it from air or any ambient gas.

The liquid handling apparatus employed in the present invention includes an open-ended conduit 21 which is preferably an automated pipette of a type similar to 10 that described in the above mentioned patents. The conduit has an open end 23 and an opposite end 25 closed by a plunger 27 which may be operated by an electrical actuator 29. A removable tip 24 is frequently used at the end of a pipette, but this is optional for the invention. The plunger 27 has a movable end 28 in sealed relation to the interior wall of conduit 21.

The purpose of the plunger 27 is to draw or expel a liquid specimen from or into the conduit 21, to a desired extent, for transfer to another container or laboratory receptacle. The plunger is connected by a rod 31 to actuator 29, which may be a stepping motor or a linear motor or magnetostrictive actuator. In all cases, the actuator responds to command signals entered on electrical line 33, moving a plunger 27 up and down to the desired extent. If very fine motion is desired, actuator 29 may be servo controlled.

In accord with the present invention, air displacement waves, such as acoustic waves are established in conduit 21. This may be achieved by an acoustic transducer, such as a miniature speaker 35 emitting pressure waves into a first hollow tube 37 which penetrates the side wall of conduit 21, thereby communicating pressure waves from the speaker into the conduit. The pressure waves are preferably acoustic waves, although non-sonic waves may also be used.

It is known that an open pipe has a natural or resonant frequency which is twice that of a closed pipe. Of course, waves introduced into the conduit are not necessarily of a resonant frequency. However, wave behavior is similar to the physics of pipes because when the conduit is closed, by contact of tip 23 with the liquid interface 17, nodes exist at opposite ends of the conduit forcing a certain vibrational mode. This vibrational mode creates a characteristic acoustic impedance which is quite different from the situation where the conduit is open. Acoustic impedance may be measured by changes in amplitude of waves within the conduit, changes in frequency, phase or measurement of the change in the quality factor, Q, of the transducer causing the vibrations. The quality factor, Q, is a measure of the loading or losses in the conduit by the excitation transducer or wave transmitter with respect to the opened or closed conduit end. Measurement of loading is a direct measurement of acoustic impedance.

An electrical sine wave oscillator 39 provides electrical excitation to the speaker 35 which acts as a pressure wave transducer. The pressure wave output frequency has no limits. Loading of the speaker 35 may be measured by a circuit having a feedback feature, such as an automatic gain control circuit, with the objective of maintaining a certain output level to the conduit. When the conduit is closed by contact with the liquid boundary, there will be a need for a change in speaker output to maintain a constant pressure wave amplitude level in conduit 21. This is sensed at the speaker 35 and a feedback signal may be sent to oscillator 39 to change its wave amplitude to maintain the desired level in the conduit. On the other hand, when the conduit is open, a different amount of work needs to be done by the speaker and so the amount of corrective feedback to the oscillator is changed.

Another means for sensing the pressure wave condition in conduit 21 is by means of a microphone 43 which communicates with conduit 21 by means of a second hollow tube 45 which penetrates the side wall of conduit 21, preferably opposite the first tube 37. Microphone 43 senses pressure waves in conduit 21, but preferably not directly to tube 37. In other words, the first and second tubes must be spaced in a manner such that pressure waves are communicated throughout the cavity not merely going directly from speaker 35 to microphone 43, but interact first in the conduit 21. Microphone 43 has an electrical output which is connected to a detector 47 which is able to measure signal level and produce an output along line 49. While the detector is indicated to be an optically read analog meter, this is only schematic. The detector is read electrically and may be an analog or digital circuit. The detector output along line 49 is fed to a signal correlation circuit 51 which correlates the detected signal to a position signal arriving along line 53 from a positioning motor 55. For example, if motor 55 is a stepper motor, each step or motor pulse represents an amount of displacement from a starting point. If the starting point of the conduit tip is known relative to reference surface 13, tip advancement can be measured to the point of impingement with the liquid boundary layer. This measurement is carried out by correlation circuit 5 and yields liquid level or height with respect to the reference surface. However, in most instances absolute starting points are not known, but once the liquid level is detected, all other positions can be related to this. Thus it is not essential to know the position of a reference surface.

Conduit 21 is formed as a bore in a cylinder 22 which is only 5-15 centimeters long with a diameter of 1-3 centimeters. Tubes 37 and 45 are also formed as bores in the same metal body, although they could be removable tubes. Speaker 35 and microphone 43 are both miniature components, only a few millimeters in size, which are removably placed into respective housings 36 and 44 forming enlarged ends of tubes 37 and 45. The dimensions mentioned herein are only exemplary. The pressure waves need not be generated by an electrical oscillator, but may be generated by mechanical motion of the conduit. For example, a stepper motor may generate pressure waves in moving the conduit toward a liquid level.

The liquid handling apparatus described above is mounted in a housing 57 which may be moved up and down as indicated in the direction of arrows A-B, by means of gear 59 or other linear positioning mechanism. Housing 57 also supports oscillator 39 and detector 47 on small cards. Motor 55 may be commanded by a command signal 61 to move up or down, incrementally, by a desired amount. For very fine positioning requirements, a servo may be employed.

When a change in acoustic impedance occurs, the level of a liquid boundary layer has been determined. It is not necessary to measure the conduit's vertical position as long as the extent of its motion is known relative to a reference liquid boundary position.

Motor 55 moves the tip 24 into contact with the liquid boundary 17. Since oscillator 39 is on continuously, a significant change in acoustic impedance within conduit 21, as measured by a detector, may be instantaneously correlated in signal correlator 51 with the vertical position of housing 57. This measurement of liquid level may be correlated with previous measurements for monitoring change in liquid level or volume.

With reference to FIG. 2, the output transducer 35, emitting pressure waves indicated by arrow C, also acts as a sensor of acoustic impedance. This is indicated schematically by arrow D wherein the loading of the output transducer may be sensed in different ways. One feedback method is by means of an automatic gain control circuit (AGC) associated with the output transducer. Other feedback methods may also be employed. AGC circuit 61 attempts to maintain a constant audio output level and sends a feedback signal along line 63 to oscillator 39. In a situation where the conduit 21 of FIG. 1 is open, there is specific loading on the output transducer 35 and a specific amount of AGC feedback. On the other hand, when the open end of the conduit makes contact with a liquid boundary, closing the conduit, the amount of energy necessary to maintain the same output level is changed, thereby requiring a different amount of AGC feedback to oscillator 39. The level of feedback may be transmitted to detector 65 and the amplitude of feedback interpreted as acoustic impedance, Z. Changes in amplitude, wavelength, frequency or phase are all related to acoustic impedance and the term "acoustic impedance" in its broadest sense is intended to encompass such changes in amplitude or wavelength or frequency or phase. The output signal taken along line 67 then indicates whether or not the conduit is open. This signal may be fed to a signal correlation circuit for determining liquid level.

With reference to FIG. 3A, an acoustic transducer 71, such as a speaker, is shown to be driven by a sine wave oscillator 73 which feeds an output signal along line 75 to an audio amplifier 77 which in turn drives the output transducer 71. The oscillator and output transducer together form a pressure wave transmitter means. The oscillator 73 may be any of the well known types of oscillators which produces a continuous sine wave signal at a desired frequency. (About 50 hertz in this example.) This frequency is preferred for noise considerations, but other frequencies may also be used, including those frequencies having wavelengths which are shorter than the length of the conduit. However, if very short wavelengths are used, i.e. much smaller than the length of the conduit, it may become more difficult to distinguish between open and closed conduit end conditions. For this reason, a frequency of 50 hertz, having a wavelength of several meters is preferred because the length of the conduit is typically only a few centimeters, usually less than 20 centimeters.

A typical oscillator may be formed from an operational amplifier 74 with feedback components 76. A typical detector circuit is shown in FIG. 3B for use in the situation where a separate detector is employed. A microphone 81 picks up a pressure wave from a tube leading to a conduit where pressure waves have been introduced by the transducer of FIG. 3A. The microphone is a miniature microphone having an output along line 83 which is connected to a filtering network, typically comprising resistors 84 and capacitors 86. The filtered signal is transmitted to an amplifier 85 where the signal level is increased and then transmitted along line 87 to a rectifier network within the block 89. The rectifier network includes diodes 82, resistors 88 and operational amplifiers 90. The function of the rectifier network is to convert the sine waves to a DC level which is transmitted along line 91 to a level comparator 93. Here a reference level 95 is measured with respect to the DC level from rectifier network 89. Comparator 93 is able to signal along line 97 whether the signal received by microphone 81 is above or below a certain level set on the threshold line 95. The threshold line may be established by calibration and corresponds to a level above or below which there is a change in the open or closed condition of the conduit. Output line 97 is connected to a signal correlation circuit as described with reference to FIG. 1. When microphone 81 picks up a signal which causes the rectifier to produce an output different from the preexisting conduit open or closed condition, the comparator 93 switches states and indicates a change in amplitude of the received signal, i.e. a change in acoustic impedance of the conduit. Instead of providing a rectifier 89, a circuit measuring changes in wave phase could have been substituted since the closing of the conduit presents a phase shift in the received waves which have been reflected from the closed end. As a general rule, changes in amplitude are easier to measure than phase changes, but in noisy environments, a phase change may be more accurate. The microphone 81 and detector, such as rectifier 89 and comparator 93, form a pressure wave receiver means.

The output transducer has been described as a speaker, but other acoustic transducers, such as piezoelectric crystals or a piston displacement means may also be used. It is possible to fashion the conduit end from a piezoelectric material such as barium titanate or piezoelectric kynar to provide a driving signal. Another means of providing the driving signal is to fabricate the displacement plunger 27 in FIG. 1 out of nickel or another suitable ferromagnetic material which is driven magnetostrictively. Such a device would produce pressure waves similar to the ones obtained from a miniature speaker. In the present invention, since the conduit may be a pipette, pipette tips which form the open end of the conduit are readily disposable after a liquid handling operation so as to avoid contamination. For this purpose, it is preferable to use a miniature speaker and microphone as the pressure wave transmitter and receiver.

Previously, relative height of a liquid level has been described as the measurement of interest. However, absolute height may also be found by placing a container of liquid on a reference surface, such as reference surface 13 in FIG. 1. The reference surface has a known vertical position, while the liquid boundary layer 17 has an unknown position. Pressure waves are directed down the movable open-ended conduit 21, while the conduit whose tip starting position is known is slowly moved toward the liquid boundary by known amounts. Pressure waves are generated in the conduit by a pressure wave transmitter, so that changes in acoustic impedance in the conduit may be measured. Acoustic impedance is monitored as the conduit is moved toward the liquid boundary layer. When there is a change in acoustic impedance, indicative of contact with the liquid boundary layer, the position of the tip is recorded relative to the reference surface. The absolute height of the liquid boundary may be computed by simple subtraction.

While the present invention has been described with respect to an automatic pipette, the same apparatus manufactured on a larger scale, would be useful in monitoring a liquid level in a chemical process tank or reservoir.

We claim:

1. Apparatus for measuring contact between a conduit and a liquid boundary comprising,
   an open-ended conduit adapted for insertion into a liquid boundary of a liquid body, said open-ended conduit being movable towards and away from said liquid body,
   pressure wave generating means directing pressure waves into said conduit for establishing a first acoustic impedance,
   insertion means for moving the open end of said open-ended conduit into said liquid boundary, thereby closing said open end and establishing a second acoustic impedance, said insertion means generating a conduit position signal,
   detector means for detecting a change in acoustic impedance during insertion of the liquid handling means into the liquid boundary from said acoustic impedance to said second acoustic impedance and for producing an electrical output signal in response thereto, and
   signal correlating means receiving said electrical output signal and said conduit position signal for indicating liquid boundary position.

2. The apparatus of claim 1 further having a first hollow tube communicating with the interior of the conduit, said pressure waves fed into said conduit via said first tube.

3. The apparatus of claim 2 further having a second hollow tube, spaced apart from the first tube, communicating with the interior of the conduit, said second hollow tube having said detector means in communication therewith.

4. The apparatus of claim 1 wherein said detector means for detecting changes in acoustic impedance comprises a circuit means for monitoring loading of the pressure wave generating means.

5. The apparatus of claim 1 wherein said pressure wave generating means comprises an oscillator connected to a speaker.

6. The apparatus of claim 3 wherein said detector means comprises a microphone having said output signal connected to a comparator means, having a reference level connected thereto, for comparing said microphone output signal to said reference level, said reference level associated with either a liquid boundary conduit insertion condition or a no insertion condition.

7. The apparatus of claim 1 wherein said conduit is a pipette and wherein said open-ended conduit is terminated in a pipette tip, the end of said conduit opposite said pipette tip having a plunger means disposed therein.

8. The apparatus of claim 1 wherein said means for inserting said open-ended conduit into said liquid boundary comprises a movable housing, the open-ended conduit having a fixed position relative to the housing, said inserting means raising and lowering the housing relative to said liquid boundary.

9. The apparatus of claim 8 wherein said insertion means for inserting the open end of said open-ended conduit into said liquid boundary comprises a motor advancing said conduit.

10. The apparatus of claim 3 wherein said first and second tubes face each other.

11. The apparatus of claim 4 wherein said pressure wave transmitter means comprises an oscillator connected to an output transducer and said detector means for detecting changes in acoustic impedance comprises a feedback loop means between the output transducer and the oscillator for generating a signal indicative of transducer output deviation and a detector means for receiving said deviation signal and indicating a deviation beyond a preset level.

12. Apparatus for measuring contact between a vertically supported pipette and a liquid in a container,
 a pipette having an open tip at an end thereof,
 means for imparting vertical motion to said pipette in a direction approaching a container with liquid therein and for generating a position signal,
 a first hollow tube communicating with the interior of the pipette,
 pressure wave transmitter means directing pressure waves down the first tube into said pipette establishing a first acoustic impedance in said open tip,
 means for detecting a second acoustic impedance and producing an electrical output signal indicative of closure of said tip, and
 signal correlating means receiving said electrical output signal and said conduit position signal for indicating liquid boundary position.

13. The apparatus of claim 12 further having a second hollow tube, spaced apart from the first tube, communicating with the interior of the pipette, said second hollow tube having a pressure wave receiver means in communication therewith, said pressure wave receiver means comprising said means for detecting changes in said acoustic impedance.

14. The apparatus of claim 12 wherein said means for detecting changes in acoustic impedance comprises a circuit means for monitoring loading of the acoustic wave transmitter means.

15. The apparatus of claim 12 wherein said pressure wave transmitter means comprises an oscillator connected to a speaker.

16. The apparatus of claim 13 wherein said pressure wave receiver means comprises a microphone having a signal output connected to a comparator means, having a reference level connected thereto, for comparing said microphone signal output to said reference level, said reference level associated with either a pipette tip with liquid contact or no contact condition.

17. The apparatus of claim 12 wherein said pipette has a plunger means disposed therein, an end thereof opposite said tip for drawing in fluid from said tip.

18. The apparatus of claim 12 wherein said means connected to the pipette for imparting vertical motion thereto comprises a movable housing, the tip having a fixed position relative to the housing, said vertical motion means raising and lowering said housing relative to a liquid container of known position and having an electrical output producing an electrical signal representing the position of the liquid.

19. The apparatus of claim 18 having a signal correlation means receiving said signal indicative of closure of said tip and said housing position signal for computing liquid height in said liquid container.

20. The apparatus of claim 14 wherein said pressure wave transmitter means comprises an oscillator connected to an output transducer and said means for monitoring loading of the transmitter means comprises a feedback loop means between the output transducer and the oscillator for generating a signal indicative of transducer output deviation, thereby indicating a change in acoustic impedance and a detector means for receiving said deviation signal and indicating a deviation beyond a preset level.

21. A method for monitoring height of a liquid boundary in a liquid container comprising,
 directing pressure waves down a movable open-ended conduit toward a liquid boundary, the liquid boundary having an unknown position relative to a reference,
 moving the conduit toward the liquid boundary by known amounts,
 monitoring acoustic impedance in the conduit,
 recording the conduit position at the location of change in the acoustic impedance of the conduit, said change occurring during the transition from an open conduit to a conduit closed by a liquid boundary, and
 correlating the conduit position at said location of change in acoustic impedance to the reference position to establish the liquid boundary height.

* * * * *